United States Patent
Buisine et al.

(10) Patent No.: US 9,120,740 B2
(45) Date of Patent: Sep. 1, 2015

(54) METHOD FOR PREPARING DIFLUOROACETIC ACID

(75) Inventors: Olivier Buisine, Saint-genis Laval (FR); Alessandro Chiovato, Anse (FR)

(73) Assignee: RHODIA OPERATIONS, Paris (FR)

( * ) Notice: Subject to any disclaimer, the term of this patent is extended or adjusted under 35 U.S.C. 154(b) by 916 days.

(21) Appl. No.: 13/381,607

(22) PCT Filed: Jun. 28, 2010

(86) PCT No.: PCT/EP2010/059142
§ 371 (c)(1),
(2), (4) Date: Jan. 31, 2012

(87) PCT Pub. No.: WO2011/000804
PCT Pub. Date: Jan. 6, 2011

(65) Prior Publication Data
US 2012/0123159 A1    May 17, 2012

(30) Foreign Application Priority Data
Jun. 30, 2009 (FR) ..................................... 09 03184

(51) Int. Cl.
C07C 51/347    (2006.01)
C07C 67/10    (2006.01)
C07C 51/09    (2006.01)

(52) U.S. Cl.
CPC ................ *C07C 67/10* (2013.01); *C07C 51/09* (2013.01)

(58) Field of Classification Search
None
See application file for complete search history.

(56) References Cited

U.S. PATENT DOCUMENTS 5,455,376 A    10/1995    Bielefeldt

FOREIGN PATENT DOCUMENTS

| EP | 0 694 523 A1 | 1/1996 |
| EP | 1 137 615 A | 10/2001 |
| JP | 6-228043 A | 8/1994 |
| WO | WO 00/35834 A1 | 6/2000 |
| WO | WO0210108 | 2/2002 |

OTHER PUBLICATIONS

International Search Report (PCT/ISA/210) issued on Aug. 16, 2010, by European Patent Office as the International Searching Authority for International Application No. PCT/EP2010/059142.
Cohn, Bergmann, The Autoxidation of 1,1-dibromo-2,2-difluoroethylene and tribromoethylene. Preparation of dibromofluor- and fluorodibromo-acetic acid, Israel Journal of Chemistry, vol. 2, No. 6, 1963, pp. 355-361, Weizmann Science Press of Israel, Jerusalem, Israel.
Gryszkiewicz-Trochimowski, E.; Sporzynski, A.; Wnuk, J. "Organic fluorine compounds in the aliphatic series. II. Derivatives of mono-, di-, and trifluoroacetic acid" Recueil des Travaux Chimiques des Pays-Bas et de la Belgique, vol. 66, pp. 419-26. (English language abstract only).
Database WPI Week 200234, Feb. 7, 2002, Thomson Scientific, London, GB (WPI database entry for previously-disclosed document WO 0210108, published Feb. 7, 2002).

*Primary Examiner* — Michael Barker
*Assistant Examiner* — Po-Chih Chen

(57) ABSTRACT

A method for preparing difluoroacetic acid is described. The method can include: reacting a difluoroacetic acid ester with an aliphatic carboxylic acid which, after transesterification, results in the formation of difluoroacetic acid and the corresponding carboxylic acid ester, the carboxylic acid being selected such that the ester of the carboxylic acid has a lower boiling point than that of difluoroacetic acid; and removing the ester of the carboxylic acid by distillation as the ester forms, thus enabling the difluoroacetic acid to be recovered.

21 Claims, No Drawings

METHOD FOR PREPARING DIFLUOROACETIC ACID

This application claims priority under 35 U.S.C. §119 of FR 0903184, filed Jun. 30, 2009, and is the United States national phase of PCT/EP2010/059142, filed Jun. 28, 2010, and designating the United States (published in the French language on Jan. 6, 2011, as WO 2011/000804 A1; the title and abstract were also published in English), each hereby expressly incorporated by reference in its entirety and each assigned to the assignee hereof.

A subject matter of the present invention is a novel process for the preparation of difluoroacetic acid.

The invention is targeted at the preparation of a high-purity difluoroacetic acid.

Several routes for accessing difluoroacetic acid exist in the literature.

One of the access routes described in EP-A 1 137 615 consists in carrying out the hydrogenation/dehalogenation of chlorodifluoroacetic acid by hydrogenation in a basic medium in the presence of in particular Raney nickel.

Difluoroacetic acid can also be prepared from chlorodifluoroacetic acid according to a gas-phase process as described in U.S. Pat. No. 5,455,376, the hydrogenation being carried out between 120° C. and 250° C. in the presence of a catalyst based on palladium/platinum and/or nickel in the metal or supported form, for example supported on alumina.

It is also known, according to JP-A 6228043, to prepare difluoroacetic acid by basic hydrolysis of an N,N-dialkyldifluoroacetamide, the latter being prepared by KF exchange of an N,N-dialkyldichloroacetamide obtained by reaction of dichloroacetyl chloride and a dialkylamine.

E. Gryskiewicz-Trochimowski et al. (Recueil des Travaux Chimiques des Pays-Bas, 1947, 66, 419-426) describe the formation of difluoroacetic acid by saponification of the methyl ester of difluoroacetic acid in the presence of water and lime.

All these processes result in difluoroacetic acid or its salt.

The problem which is presented is that it is very difficult to purify difluoroacetic acid obtained in aqueous solution as this is a product which is soluble in water and, under these conditions, more difficult to separate by distillation.

Furthermore, a description is given, in WO 02/10108, of a process for the preparation of a fluorinated ester $R^d$—O—CO—$R^{cf}$ and of a fluorinated alcohol $R^{af}R^{bf}$CHOH according to a conventional transesterification reaction of a fluorinated ester $R^{af}R^{bf}$CH—O—CO—$R^{cf}$ with an alcohol $R^d$OH; the alcohol formed being distilled off as it is formed.

H. Cohn et al. (Israel Journal of Chemistry, 2, 1964, 355-361) describe the preparation of perhalogenated acids (bromodifluoroacetic acid, dibromofluoroacetic acid) by transesterification of the corresponding ethyl esters with formic acid, ethyl formate being distilled off as it is formed. However, the teaching relates only to perhalogenated acids.

The objective of the present invention is to provide a simple process for the preparation of difluoroacetic acid which makes it possible to obtain it pure.

The term "high-purity" is understood to mean, in the present text, a difluoroacetic acid having a purity of greater than or equal to 95% by weight, preferably of greater than or equal to 98% by weight and more preferably of greater than or equal to 99% by weight.

There has now been found, and it is this which constitutes the subject matter of the present invention, a process for the preparation of difluoroacetic acid, characterized in that it comprises:

the reaction of a difluoroacetic acid ester with an aliphatic carboxylic acid, resulting, subsequent to a transesterification reaction, in the formation of difluoroacetic acid and the corresponding carboxylic acid ester, the carboxylic acid being chosen so that the ester of said carboxylic acid has a boiling point below that of difluoroacetic acid, the removal by distillation of the ester of said carboxylic acid as it is formed, thus making it possible to recover the difluoroacetic acid.

The reaction scheme of the process of the invention is given below in order to facilitate understanding of the invention without, however, binding the scope of the invention to this scheme.

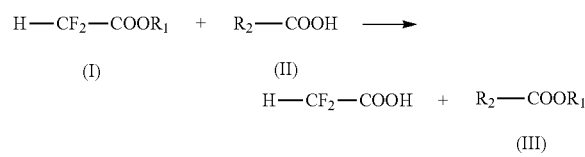

In accordance with the process of the invention, a difluoroacetic acid of high purity of at least 95% is obtained, which implies that subsequent purification operations are possible but not necessary.

This good purity results from the fact that the degree of conversion of the difluoroacetic acid ester of formula (I) is virtually 100% and that the product coproduced by the reaction, namely the carboxylic acid ester of formula (III), is removed as it is formed.

The difluoroacetic acid obtained according to the process of the invention is anhydrous with a water content advantageously of less than 1% by weight.

A difluoroacetic acid ester is thus involved in the process of the invention, the hydrocarbon group $R_1$ of the ester functional group $COOR_1$ of which is determined so that it results in a carboxylic acid ester (III) which exhibits a boiling point below that of difluoroacetic acid.

This group $R_1$ is advantageously an alkyl group having a low carbon condensation, for example of 1 to 4 carbon atoms, but it is preferable for $R_1$ to represent a methyl, ethyl, propyl or isopropyl group.

Thus, preferably, the difluoroacetic acid esters correspond to the following formula:

In said formula:

$R_1$ representing an alkyl group having from 1 to 4 carbon atoms, preferably 1 or 2 carbon atoms.

The compounds of formula (I) preferably employed in the process of the invention are alkyl esters, preferably the methyl or ethyl ester of difluoroacetic acid.

The difluoroacetic acid esters of formula (I) are compounds which are available commercially or which can easily be prepared according to the processes described in the literature.

A favored access route consists in reacting an alcohol $R_1$OH with difluoroacetyl fluoride with formula H—$CF_2$—COF. Reference may in particular be made to the preparation described in EP-A 0 694 523.

As regards the source of protons making it possible to carry out the transesterification, it is symbolized by the formula (II), $R_2$—COOH, the hydrocarbon group $R_2$ bonded to the acid functional group COOH of which is determined so that it results in a carboxylic acid ester (III) which exhibits a boiling point below that of difluoroacetic acid.

The aliphatic carboxylic acids preferably chosen to be employed in the process of the invention correspond to the following formula:

$$R_2\text{—COOH} \quad \text{(II)}$$

In said formula:

$R_2$ representing a hydrogen atom, an alkyl group having 1 or 2 carbon atoms or a haloalkyl group having 1 carbon atom, 1 to 3 hydrogen atoms of which can be replaced by a halogen atom.

The term "halogen atom" is understood to mean a fluorine, chlorine or bromine atom.

Recourse is more particularly had, as compounds of formula (II), to formic acid, acetic acid, trifluoroacetic acid, monochloroacetic acid, dichloroacetic acid or trichloroacetic acid.

Among the abovementioned compounds, formic acid is preferred.

In accordance with the invention, the difluoroacetic acid ester of formula (I) and the aliphatic carboxylic acid of formula (II) are reacted in proportions such that the ratio of the number of moles of difluoroacetic acid ester to the number of moles of aliphatic carboxylic acid varies between 0.8 and 1.2 and is preferably equal to 1.

The transesterification reaction is preferably carried out in the absence of catalysts but the invention does not exclude the use of a catalyst conventionally used for this type of reaction, namely a catalyst of strong acid type. Mention may in particular be made of sulfuric acid or p-toluenesulfonic acid.

Mention may be made, as other examples of protic acid catalysts which are also suitable, of the resins composed of a polystyrene backbone which carries sulfonic groups and more particularly of the resins sold under various trade names: Amberlyst 15, Amberlyst or Amberlyst 36, or of the perfluorinated resins carrying sulfonic groups and more particularly of Nafion, which is a copolymer of tetrafluoroethylene and perfluoro[2-(fluorosulfonylethoxy)propyl] vinyl ether.

The amount of catalyst employed, expressed as protons H⁻ with respect to the difluoroacetic acid ester of formula (I), generally represents from 0.1 to 10 mol %.

The process which is the subject matter of the present invention comprises at least one stage of mixing the difluoroacetic acid ester of formula (I) and the aliphatic carboxylic acid of formula (II) and one distillation stage designed in order to obtain:

at the distillation bottom, the expected difluoroacetic acid, and, at the distillation top, a gas phase comprising the ester of formula (III) formed.

A first embodiment of the invention consists in carrying out the process of the invention batchwise.

The process of the invention comprises an operation in which the difluoroacetic acid ester of formula (I) and the aliphatic carboxylic acid of formula (II) are mixed by bringing the two reactants into contact preferably at ambient temperature (generally between 15° C. and 25° C.) and then the reaction mixture, kept at atmospheric pressure, is brought to a temperature such that the carboxylic acid ester of formula (III) is distilled off as it is formed.

The mixture is distilled while collecting, at the distillation top, the ester of formula (III) and optionally one of the two reactants in excess and, at the distillation bottom, the difluoroacetic acid.

The reactants are introduced, separately or as a mixture, into a reactor equipped with stirring and heating means and surmounted by a distillation column.

In order to carry out the distillation, heat can be supplied to the column bottom in particular by circulation of a heat-transfer fluid in the jacket of a reactor or another form consists in heating, in a heat exchanger, a fraction of the reaction mixture withdrawn at the distillation bottom; the withdrawn stream passes from the bottom upwards through a heat exchanger and is introduced at the exchanger outlet laterally into the lower part of the distillation column. The circulation of the stream can be natural or forced using a pump.

The distillation operation is targeted at obtaining, at the bottom, the difluoroacetic acid devoid of the ester of formula (III), which is removed at the distillation top.

In the case where one of the reactants is in excess, it is distilled after distillation of the ester of formula (III).

The distillation of the ester of formula (III) is carried out at a temperature in the reboiler chosen so that the temperature is sufficient to obtain, at the column top, the boiling point of the ester of formula (III).

The distillation is preferably carried out at atmospheric pressure. However, a pressure slightly lower than or greater than atmospheric pressure is also possible.

In the preferred case of the use of formic acid or trifluoroacetic acid as carboxylic acid, the temperature in the reboiler remains below 100° C. at atmospheric pressure and is preferably between 50 and 100° C.

The distillation is carried out using a conventional distillation column.

A person skilled in the art is fully able to choose the means to be employed according to the compounds to be separated.

The following will simply be restated. The size (in particular the diameter) of the distillation columns depends on the circulating stream and on the internal pressure. They will thus mainly be designed according to the flow rate of mixture to be treated. The internal parameter which is the number of theoretical stages is determined in particular by the purity of the starting compound and the purity of the product which has to be obtained at the distillation top.

It will be specified that the columns can be packed without distinction with plates or with stacked packing, as is fully known to a person skilled in the art.

The plant being determined, a person skilled in the art adjusts the operating parameters of the column.

Thus, the distillation column can advantageously but not limitingly be a column having the following specifications:

number of theoretical stages: from 1 to 20, preferably from 5 to 10, reflux ratio R of between 0 and 10, preferably between 1 and 5.

At the column bottom, a distillation concentrate comprising difluoroacetic acid is recovered and, at the column top, a gas phase composed of the ester of formula (III) is recovered.

This gas phase is cooled and is converted into the liquid form by cooling to a temperature, for example, of between −10° C. and 25° C., preferably between 0° C. and 10° C.

This operation is carried out by passing through a condenser which is a conventional device, for example a tubular exchanger supplied with water or with a fluid held at a temperature in the vicinity of the chosen cooling temperature.

The condensed stream is introduced laterally at the distillation column top in order to provide for the reflux of the column.

The difluoroacetic acid with a very good chemical purity is recovered at the distillation bottom.

In the case where a transesterification catalyst is employed, the latter is also found in the distillation bottom and there is cause to separate the difluoroacetic acid from this medium by an additional distillation operation at a temperature of 132° C.-133° C. when the distillation is carried out at atmospheric pressure.

Another embodiment of the invention consists in carrying out the process of the invention continuously and in carrying out a reactive distillation, which means that the mixing and the distillation are carried out in a distillation column.

This embodiment of the invention is preferred.

The distillation column is fed continuously using the two reactants, namely the difluoroacetic acid ester of formula (I) and the aliphatic carboxylic acid of formula (II).

More specifically, the feeding of the difluoroacetic acid ester is preferably carried out in the lower part of the column.

The feeding of the aliphatic carboxylic acid of formula (II) is preferably carried out in the upper part of the column.

The reaction region is preferably located at midheight of the column.

In accordance with the process of the invention, the ester of formula (III) is distilled off as it is formed and the difluoroacetic acid is recovered at the column bottom.

The reflux of the column is provided by the liquid stream recovered subsequent to the condensation of the ester of formula (III) and returned laterally to the column.

All the distillation conditions, in particular temperature and pressure, are as mentioned above for the batchwise load.

The difluoroacetic acid formed is withdrawn at the column bottom.

In the case where a transesterification catalyst is employed, the latter is introduced in the solid form (resins or supported acid) into the reactive part of the distillation column.

The difluoroacetic acid is recovered at the column bottom and separation of the catalyst is therefore unnecessary.

The process of the invention is advantageously carried out in an apparatus capable of withstanding the corrosion brought about by the difluoroacetic acid.

To this end, materials are chosen for the part in contact with the reaction medium which are resistant to corrosion, advantageously enameled steels or stainless steels, such as austenitic steels [Robert H. Perry et al., *Perry's Chemical Engineers' Handbook*, Sixth Edition (1984), page 23-44] and more particularly stainless steels 304, 304 L, 316 or 316 L.

Use is made of a steel having a nickel content of at most 22% by weight, preferably of between 6 and 20% by weight and more preferably of between 8 and 14% by weight.

The steels 304 and 304 L have a nickel content varying between 8 and 12% and the steels 316 and 316 L have a nickel content varying between 10 and 14%.

Recourse is more particularly had to the steels 316 L.

All of the various stages of the process of the invention can thus be carried out continuously or batchwise.

Implementational examples of the invention are given below. These examples are given by way of illustration and without a limiting nature.

In the examples, the degree of conversion and the yield obtained are defined.

The degree of conversion (DC) corresponds to the ratio of the number of mols of substrate [difluoroacetic acid ester of formula (I)] converted to the number of mols of substrate [difluoroacetic acid ester of formula (I)] charged.

The yield (RY) corresponds to the ratio of the number of mols of product formed (difluoroacetic acid) to the number of mols of substrate [difluoroacetic acid ester of formula (I)] charged.

The various analyses are carried out by $^1$H NMR and $^{19}$F NMR.

EXAMPLE 1

Ethyl difluoroacetate (15 g; 0.121 mol) is brought together with formic acid (9 g, 0.196 mol, 1.6 equivalents) and 0.1 g of 98% by weight sulfuric acid in a glass reactor surmounted by a distillation column.

The reaction medium is brought to the temperature of 70° C. at atmospheric pressure.

Reflux appears and total reflux is maintained until the temperature at the column top has stabilized at 55° C.

A fraction is then collected so as to keep a temperature at the column top constant at 55° C.

A fraction of 9 g of ethyl formate is obtained.

Analysis of the reaction medium shows that all of the ethyl difluoroacetate has been converted to difluoroacetic acid (DC=100%).

The difluoroacetic acid obtained has a purity of greater than 98% by weight.

The yield (RY) is 95%.

EXAMPLE 2

Ethyl difluoroacetate (20 g 0.161 mol) is brought together with formic acid (7.4 g, 0.161 mol, 1 equivalent) and 0.1 g of 98% by weight sulfuric acid in a glass reactor surmounted by a distillation column.

The reaction medium is brought to the temperature of 70° C. at atmospheric pressure and a distillation fraction is then collected, so as to keep the temperature at the column top constant at 55° C.

A fraction of 12 g of ethyl formate is obtained.

Analysis of the reaction medium shows that all of the ethyl difluoroacetate has been converted to difluoroacetic acid (DC=100%).

The medium is then distilled at atmospheric pressure.

A fraction (w=14.8 g) having a boiling point of 133° C. is recovered.

The difluoroacetic acid obtained has a purity of greater than 98% by weight.

The yield (RY) is 96%.

EXAMPLE 3

Ethyl difluoroacetate (60 g, 0.484 mol) is brought together with trifluoroacetic acid (56 g, 0.484 mol, 1 equivalent) in a glass reactor surmounted by a distillation column.

The reaction medium is brought to the temperature of 85° C. at atmospheric pressure.

Ethyl trifluoroacetate is distilled off while keeping the temperature of the distillation top at 63° C.

A fraction of 69 g of ethyl trifluoroacetate is obtained.

All of the ethyl difluoroacetate was consumed (DC=100%) and the difluoroacetic acid obtained at the distillation bottom has a purity of 99.5% by weight.

The yield (RY) is greater than 99%.

The invention claimed is:

1. A process for the preparation of difluoroacetic acid, the process comprising:
   reacting a difluoroacetic acid ester with an aliphatic carboxylic acid, resulting, subsequent to a transesterification reaction, in the formation of difluoroacetic acid and an aliphatic carboxylic acid ester, the carboxylic acid being chosen so that said aliphatic carboxylic acid ester has a boiling point below the boiling point of difluoroacetic acid; and removing said aliphatic carboxylic acid ester by distillation as it is formed, thus making it possible to recover the difluoroacetic acid.

2. The process as claimed in claim 1, wherein the difluoroacetic acid ester corresponds to the following formula:

$$H-CF_2-COOR_1 \tag{I}$$

wherein:
$R_1$ represents an alkyl group having from 1 to 4 carbon atoms.

3. The process as claimed in claim 2, wherein the difluoroacetic acid ester is a methyl ester or an ethyl ester of difluoroacetic acid.

4. The process as claimed in claim 1, wherein the aliphatic carboxylic acid corresponds to the following formula:

$$R_2-COOH \tag{II}$$

wherein:
$R_2$ represents a hydrogen atom, an alkyl group having 1 or 2 carbon atoms, or a haloalkyl group having 1 carbon atom and 1 to 3 halogen atoms.

5. The process as claimed in claim 4, wherein the aliphatic carboxylic acid is formic acid, acetic acid, trifluoroacetic acid, monochloroacetic acid or trichloroacetic acid.

6. The process as claimed in claim 1, wherein the transesterification reaction is carried out in the presence of a protic acid catalyst.

7. The process as claimed in claim 6, wherein the protic acid catalyst is selected from the group consisting of a sulfuric acid catalyst, a p-toluenesulfonic acid catalyst and a sulfonic resin catalyst.

8. The process as claimed in claim 1, wherein the difluoroacetic acid has a purity of greater than or equal to 95%.

9. The process as claimed 8, wherein the purity is between 99% and 99.5%.

10. The process according to claim 1, wherein the difluoroacetic acid ester corresponds to the following formula:

$$H-CF_2-COOR_1 \tag{I}$$

wherein:
$R_1$ represents an alkyl group having from 1 to 4 carbon atoms; and the aliphatic carboxylic acid corresponds to the following formula:

$$R_2-COOH \tag{II}$$

wherein:
$R_2$ represents a hydrogen atom, an alkyl group having 1 or 2 carbon atoms, or a haloalkyl group having 1 carbon atom and 1 to 3 halogen atoms; and the aliphatic carboxylic acid ester corresponds to the following formula:

$$R_2-COOR_1 \tag{III}$$

11. The process as claimed in claim 10, wherein the difluoroacetic acid ester of formula (I) and the aliphatic carboxylic acid of formula (II) are reacted in proportions such that a ratio of the number of moles of difluoroacetic acid ester to the number of moles of aliphatic carboxylic acid is between 0.8 and 1.2.

12. The process as claimed in claim 11, wherein the ratio of the number of moles of difluoroacetic acid ester to the number of moles of aliphatic carboxylic acid is equal to 1.

13. The process as claimed in claim 10, wherein the process comprises at least one stage of mixing the difluoroacetic acid ester of formula (I) and the aliphatic carboxylic acid of formula (II) and one distillation stage designed in order to obtain:
at the distillation bottom, the expected difluoroacetic acid, and, at the distillation top, a gas phase comprising the ester of formula (III) formed.

14. The process as claimed in claim 13, wherein the process comprises an operation in which the difluoroacetic acid ester of formula (I), as a first reactant, and the aliphatic carboxylic acid of formula (II), as a second reactant, are mixed by bringing the two reactants into contact, resulting in a reaction mixture, and then the reaction mixture, kept at atmospheric pressure, is brought to a temperature such that the carboxylic acid ester of formula (III) is distilled off as it is formed.

15. The process as claimed in claim 14, wherein the two reactants are brought into contact at ambient temperature.

16. The process as claimed in claim 13, wherein the reactants are introduced, separately or as a mixture, into a reactor equipped with stirring and heating means and surmounted by a distillation column.

17. The process as claimed in claim 13, wherein a reactive distillation is carried out and the mixing and the distillation are carried out in a distillation column.

18. The process as claimed in claim 17, wherein the distillation column is fed continuously using the difluoroacetic acid ester of formula (I) and the aliphatic carboxylic acid of formula (II).

19. The process as claimed in claim 18, wherein the difluoroacetic acid ester of formula (I) is fed into a lower part of the distillation column.

20. The process as claimed in claim 18, wherein the aliphatic carboxylic acid of formula (II) is fed into an upper part of the distillation column.

21. The process as claimed in claim 7, wherein a reflux of the column is provided by a liquid stream recovered subsequent to condensation of the ester of formula (III) and returned laterally to the column.

* * * * *